United States Patent
Mayhall et al.

(10) Patent No.: US 7,112,559 B1
(45) Date of Patent: Sep. 26, 2006

(54) THICKENED QUATERNARY AMMONIUM COMPOUND SANITIZER

(75) Inventors: Jennifer Mayhall, Belews Creek, NC (US); Margaret Bissell, Amherst, VA (US); Anna Starobin, Greensboro, NC (US)

(73) Assignee: Ecolab Inc., St. Paul, MN (US)

( * ) Notice: Subject to any disclaimer, the term of this patent is extended or adjusted under 35 U.S.C. 154(b) by 0 days.

(21) Appl. No.: 11/079,693

(22) Filed: Mar. 14, 2005

(51) Int. Cl.
C11D 1/62 (2006.01)
C11D 3/37 (2006.01)
C11D 3/44 (2006.01)

(52) U.S. Cl. .................. 510/131; 510/130; 510/138; 510/382; 510/384; 510/391; 510/398; 510/504; 510/432

(58) Field of Classification Search ........... 510/138, 510/130, 131, 382, 384, 391, 398, 432, 504
See application file for complete search history.

(56) References Cited

U.S. PATENT DOCUMENTS

| | | | |
|---|---|---|---|
| 3,816,407 A | 6/1974 | Zell | |
| 3,956,510 A | 5/1976 | Molnar | |
| 4,792,415 A | 12/1988 | Colegrove | |
| 5,288,486 A | 2/1994 | White | |
| 5,417,968 A * | 5/1995 | Staats | 424/78.07 |
| 5,531,984 A | 7/1996 | Staats | |
| 5,661,170 A | 8/1997 | Chodosh | |
| 5,750,579 A * | 5/1998 | Kamishita et al. | 514/772.6 |
| 5,827,870 A * | 10/1998 | Chodosh | 514/390 |
| 5,951,993 A | 9/1999 | Scholz | |
| 5,968,986 A | 10/1999 | Dyer | |
| 5,994,383 A | 11/1999 | Dyer | |
| 5,997,893 A * | 12/1999 | Jampani et al. | 424/405 |
| 6,013,677 A | 1/2000 | Dyer | |
| 6,022,549 A | 2/2000 | Dyer | |
| 6,022,551 A * | 2/2000 | Jampani et al. | 424/405 |
| 6,087,400 A * | 7/2000 | Dyer et al. | 514/643 |
| 6,090,395 A | 7/2000 | Asmus | |
| 6,114,396 A | 9/2000 | Rens | |
| 6,136,771 A | 10/2000 | Taylor | |
| 6,209,751 B1 | 4/2001 | Goodin | |
| 6,248,343 B1 * | 6/2001 | Jampani et al. | 424/405 |
| 6,258,370 B1 | 7/2001 | Behrends | |
| 6,279,777 B1 | 8/2001 | Goodin | |
| 6,344,218 B1 * | 2/2002 | Dodd et al. | 424/605 |
| 6,479,039 B1 | 11/2002 | Dyer | |
| 6,488,948 B1 * | 12/2002 | Danieli | 424/404 |
| 6,645,510 B1 * | 11/2003 | Coury et al. | 424/401 |
| 6,656,456 B1 * | 12/2003 | Dodd et al. | 424/67 |
| 6,723,689 B1 * | 4/2004 | Hoang et al. | 510/130 |
| 6,846,846 B1 * | 1/2005 | Modak et al. | 514/722 |
| 2001/0016589 A1 | 8/2001 | Modak | |
| 2001/0036963 A1 | 11/2001 | Behrends | |

FOREIGN PATENT DOCUMENTS

| | | |
|---|---|---|
| CN | 1258448 | 7/2000 |
| DE | 1288747 | 2/1969 |
| DE | 2338386 | 9/1974 |
| DE | 3519557 | 12/1985 |
| DE | 19537782 | 4/1997 |
| DE | 19646726 | 5/1998 |
| EP | 0343605 | 12/1992 |
| GB | 2171013 | 8/1986 |
| JP | 6279214 | 10/1994 |
| JP | 2001316209 | 11/2001 |
| WO | WO97/00667 | 1/1997 |
| WO | WO97/21348 | 6/1997 |
| WO | WO00/54587 | 9/2000 |
| WO | WO01/41567 | 6/2001 |

OTHER PUBLICATIONS

Dermal Defense™ Automated Infraared Liquid Dispensing System Product Catalogue, Tri-anim, 1 page.
Dermal Defense™ Website Information, http://www.dermaldefense.com, Jan. 5, 2004, 7 pages.
"Skinvisible receives Largest Single Order for Antimicrobial Hand Sanitizer In the Battle Against the Flu Virus", Dec. 17, 2003, http://news.corporate.findlaw.com/prnewswire/20031217/17dec2003142922,html, 2 pgs.

* cited by examiner

*Primary Examiner*—Charles Boyer
(74) *Attorney, Agent, or Firm*—Andrew D. Sorensen; Anneliese S. Mayer

(57) ABSTRACT

The invention pertains to a thickened rinseless hand sanitizer composition comprising a quaternary ammonium compound. The invention also pertains to a method of applying to the skin of a human a thickened rinseless hand sanitizer composition that comprises a quaternary ammonium compound that evaporates off the skin. The invention further pertains to a thickened rinseless hand sanitizer composition comprising a quaternary ammonium compound with additional functional ingredients. Finally, the invention pertains to a thickened rinseless hand sanitizer composition comprising a quaternary ammonium compound composed of food additive ingredients.

11 Claims, No Drawings

THICKENED QUATERNARY AMMONIUM COMPOUND SANITIZER

FIELD OF THE INVENTION

The invention pertains to a thickened rinseless hand sanitizer composition comprising a quaternary ammonium compound. The invention also pertains to a method of applying to the skin of a human a thickened rinseless hand sanitizer composition that comprises a quaternary ammonium compound that evaporates off the skin. The invention further pertains to a thickened rinseless hand sanitizer composition comprising a quaternary ammonium compound with additional functional ingredients. Finally, the invention pertains to a thickened rinseless hand sanitizer composition comprising a quaternary ammonium compound composed of food additive ingredients.

BACKGROUND

Proper hand care has long been cited as an effective way of reducing the spread of germs, diseases, and other contaminants. Proper hand care is especially important in industries where bacteria are particularly problematic such as the health care industries, patient care industries, and the food and beverage industries. Typically, hand care has involved the washing of hands with soap followed by rinsing the hands with water to remove the soap. However, antimicrobial products that do not require a water rinse because they evaporate off, also referred to as rinseless hand sanitizers, have become popular in recent years as another way of sanitizing hands. When such a rinseless hand sanitizer is used, the user applies the product to the hands and rubs the hands together so that the product eventually either evaporates or is absorbed into the skin. These antimicrobial products come in the form of lotions, gels, and foams. Antimicrobial agents that may be used in such products include alcohols, trichlorohydroxy diphenyl ether (Triclosan), parachlorometaxylenol (PCMX), and quaternary ammonium compounds.

When alcohol is present as the antimicrobial agent, it is usually present from about 60 wt. % to about 90 wt. % and is usually present in a gel or liquid. However, alcohol based gels or liquids often dry out the user's hands which leads to skin irritation and less frequent use by the user. Quaternary ammonium compounds have been developed as a way of sanitizing hands without drying skin the way alcohol sanitizers do. Currently, quaternary ammonium compound based rinseless hand sanitizers have been used as foams or water thin liquids because the compositions are not viscous enough to be used as a gel without running off of the user's hands. Further, the thickeners used to thicken alcohol based hand sanitizer gels are often incompatible with a quaternary ammonium compound in that they chemically react with the quat, thereby reducing the antimicrobial activity of the quat and generating unwanted byproducts. Therefore, a need exists for a thickened quaternary ammonium compound sanitizer that effectively sanitizes hands without the drying effects of an alcohol based sanitizer, can be used as a gel, and provides containment on the hands, where containment refers to a product remaining on a user's hands and not running off.

In the food and beverage industry, employees touch food on a regular basis. Therefore, a need exists for a thickened quaternary ammonium compound sanitizer that is composed of food additive ingredients so that employees are encouraged to use the hand sanitizer when working with food and the hand sanitizer may be safely consumed by humans and mammals.

SUMMARY

Surprisingly, it has been discovered that including a thickener in a rinseless hand sanitizer composition comprising a quaternary ammonium compound produces an effective thickened rinseless hand sanitizer composition that can be used as a gel. This composition can be used as part of a method of sanitizing the skin of a human or mammal. The sanitizer composition may include additional functional ingredients. It has also been discovered that the thickened quaternary ammonium compound can be made using food additive ingredients that can be consumed safely by humans or mammals.

These and other embodiments will be apparent to those of skill in the art and others in view of the following detailed description of some embodiments. It should be understood, however, that this summary, and the detailed description illustrate only some examples of various embodiments, and are not intended to be limiting to the invention as claimed.

DETAILED DESCRIPTION OF SOME EMBODIMENTS

As discussed above, the invention generally relates to a thickened rinseless hand sanitizer composition comprising a quaternary ammonium compound. In one embodiment, the composition includes a quaternary ammonium compound, a thickener, and a solvent. In another embodiment, the invention includes a method of sanitizing the skin of a human or mammal using a thickened rinseless hand sanitizer composition comprising a quaternary ammonium compound. In yet another embodiment, the invention includes a thickened rinseless hand sanitizer composition comprising a quaternary ammonium compound that includes additional functional ingredients that enhance the effectiveness of the composition. Finally, the invention includes a thickened rinseless hand sanitizer composition comprising a quaternary ammonium compound that is composed of food additive ingredients that can safely be administered to or consumed by humans or mammals.

Surprisingly, it has been discovered that adding a thickener to a quaternary ammonium compound sanitizer composition provides for a thickened skin sanitizer that does not need to be rinsed off and does not cause the skin irritation experienced with an alcohol based sanitizer composition. It has also been discovered that such thickened quaternary ammonium compounds can be made using food additive ingredients. This is particularly advantageous for employees in the food and beverage industry who work with food regularly.

Definitions

For the following defined terms, these definitions shall be applied, unless a different definition is given in the claims or elsewhere in this specification.

As used herein, the phrase "a rinseless hand sanitizer composition," or "rinseless hand sanitizer" refers to a composition that is effective at killing bacteria on human skin when the user applies the composition to the hands and rubs the hands together so that the composition eventually either evaporates or is absorbed into the skin. The phrase "a rinseless hand sanitizer composition" also refers to a composition that does not need to be rinsed off of skin. Included within this definition are rinseless hand sanitizer compositions that evaporate rapidly off of the user's hands.

As used herein, the phrase "substantially free of an alcohol sanitizer" is defined as a composition that has less than about 30 wt. % of the total use composition of an alcohol. The phrase "substantially free of an alcohol sanitizer" is also defined as a composition that does not include an antimicrobially effective amount of an alcohol. The phrase "substantially free of an alcohol sanitizer" does apply to compositions that have a hydroxyl group but do not exhibit antimicrobial properties. The phrase "substantially free of an alcohol sanitizer" does include a composition that includes an alcohol in amount below 30 wt. % that provides additional functional benefits for example, an alcohol that serves as a solvent or a drying time enhancer.

Food Additive—In the food and beverage industry, it may be desirable that any composition or chemical that comes into contact with foods and beverages, including hand and skin sanitizer compositions, be suitable for human consumption such that when the composition or chemical comes into direct, indirect, or incidental contact with the food or beverage, it does not render the food or beverage unfit for consumption by humans or mammals. "Direct, indirect, or incidental contact" means that the food or beverage acquires an amount of the sanitizer composition. "Food or beverage" as used in this application means any substance ingested by humans or mammals including liquid, solid, semisolid, composite comestible material in the form of water, carbonated beverage, a food, juice, sports beverage, snack, edible container, or carrier. As used herein, in one embodiment, the term "food additive" refers to composition that when a food or beverage comes into direct, indirect, or incidental contact with the composition, it does not render the food or beverage unfit for consumption by humans or mammals. In an embodiment, the term "food additive" means that a composition or chemical may be safely administered to humans and mammals. In an embodiment, the term "food additive" means that the food additive compositions or chemicals, when combined together to make the compositions of the invention, preferably both sanitize skin and pass the stringent guidelines of the Federal regulations.

All numeric values are herein assumed to be modified by the term "about," whether or not explicitly indicated. The term "about" generally refers to a range of numbers that one of skill in the art would consider equivalent to the recited value (i.e., having the same function or result). In many instances, the term "about" may include numbers that are rounded to the nearest significant figure.

Weight percent, percent by weight, % by weight, wt %, and the like are synonyms that refer to the concentration of a substance as the weight of that substance divided by the weight of the composition and multiplied by 100.

The recitation of numerical ranges by endpoints includes all numbers subsumed within that range (e.g. 1 to 5 includes 1, 1.5, 2, 2.75, 3, 3.80, 4 and 5).

As used in this specification and the appended claims, the singular forms "a," "an," and "the" include plural referents unless the content clearly dictates otherwise. Thus, for example, reference to a composition containing "a compound" includes a mixture of two or more compounds. As used in this specification and the appended claims, the term "or" is generally employed in its sense including "and/or" unless the content clearly dictates otherwise.

The use of the term "antimicrobial" in this application does not mean that any resulting products are approved for use as an antimicrobial agent.

Quaternary Ammonium Compound

The term "quaternary ammonium compound" or "quat" generally refers to any composition with the formula

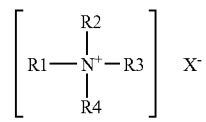

where $R_1$–$R_4$ are alkyl groups that may be alike or different, substituted or unsubstituted, saturated or unsaturated, branched or unbranched, and cyclic or acyclic and may contain ether, ester, or amide linkages; they may be aromatic or substituted aromatic groups. $X^-$ is an anionic counterion. Certain quats are known to have antimicrobial activity. Accordingly, any quaternary ammonium compound with antimicrobial activity can be used in the composition of the invention.

Depending on the nature of the R group, the anion, and the number of quaternary nitrogen atoms present, the antimicrobial quats may be classified into one of the following categories: (1) monoalkyltrimethyl ammonium salts; (2) monoalkyldimethylbenzyl ammonium salts; (3) dialkyldimethyl ammonium salts; (4) heteroaromatic ammonium salts; (5) polysubstituted quaternary ammonium salts; (6) bis-quaternary ammonium salts; and (7) polymeric quaternary ammonium salts. Each category will be discussed herein.

Monoalkyltrimethyl ammonium salts contain one R group that is a long-chain alkyl group, and the remaining R groups are short-chain alkyl groups, such as methyl or ethyl groups. Some non-limiting examples of monoalkyltrimethyl ammonium salts include cetyltrimethylammonium bromide, commercial available as Rhodaquat M242C/29 from Rhodia (Laurenceville, Ga.) and Dehyquart A from Henkel Corp. (Cincinnati, Ohio); alkyltrimethyl ammonium chloride, commercially available as Arquad 16 from Akzo Nobel Chemicals Inc. (Chicago, Ill.); alkylaryltrimethyl ammonium chloride; and cetyldimethyl ethylammonium bromide, commercially available as Ammonyx DME from Stepan Co. (Northfield, Ill.), and Bretol from Zeeland Chemical Inc. (Zeeland, Mich.).

Monoalkyldimethylbenzyl ammonium salts contain one R group that is a long-chain alkyl group, a second R group that is a benzyl radical, and the two remaining R groups are short-chain alkyl groups, such as methyl or ethyl groups. Monoalkyldimethylbenzyl ammonium salts are generally compatible with nonionic surfactants, detergent builders, perfumes, and other ingredients. Some non-limiting examples of monoalkyldimethylbenzyl ammonium salts include alkyldimethylbenzyl ammonium chlorides, commercially available as BTC 824 from Stepan Company (Northfield, Ill.), Hyamine 3500 from Lonza Inc. (Fair Lawn, N.J.), and Barquat® MB-80 from Lonza Inc. (Fair Lawn, N.J.); and benzethonium chloride, commercially available as Lonzagard, from Lonza Inc. (Fair Lawn, N.J.). Additionally, the monoalkyldimethylbenzyl ammonium salts may be substituted. Non-limiting examples of such salts include dodecyldimethyl-3,4-dichlorobenzyl ammonium chloride. Finally, there are mixtures of alkyldimethylbenzyl and alkyldimethyl substituted benzyl (ethylbenzyl) ammonium chlorides commercially available as BTC 2125M from Stepan Company (Northfield, IL), and Barquat 4250 from Lonza Inc. (Fair Lawn, N.J.).

Dialkyldimethyl ammonium salts contain two R groups that are long-chain alkyl groups, and the remaining R groups are short-chain alkyl groups, such as methyl groups. Some non-limiting examples of dialkyldimethyl ammonium salts include didecyldimethyl ammonium halides, commercially available as Bardac 22 from Lonza Inc. (Fair Lawn, N.J.); didecyl dimethyl ammonium chloride commercially available as Bardac™ 2250 or 2280 from Lonza Inc. (Fair Lawn, N.J.); dioctyl dimethyl ammonium chloride, commercially available as Bardac™ LF and Bardac™ LF-80 from Lonza Inc. (Fair Lawn, N.J.); and octyl decyl dimethyl ammonium chloride sold as a mixture with didecyl and dioctyl dimethyl ammonium chlorides, commercially available as Bardac™ 2050 and 2080 from Lonza Inc. (Fair Lawn, N.J.).

Heteroaromatic ammonium salts contain one R group that is a long-chain alkyl group, and the remaining R groups are provided by some aromatic system. Accordingly, the quaternary nitrogen to which the R groups are attached is part of an aromatic system such as pyridine, quinoline, or isoquinoline. Some non-limiting examples of heteroaromatic ammonium salts include cetylpyridinium halide, commercially available as Sumquat 6060/CPC from Zeeland Chemical Inc. (Zeeland, Mich.); 1-[3-chloroalkyl]-3,5,7-triaza-1-azoniaadamantane, commercially available as Dowicil 200 from The Dow Chemical Company (Midland, Mich.); and alkyl-isoquinolinium bromide.

Polysubstituted quaternary ammonium salts are a monoalkyltrimethyl ammonium salt, monoalkyldimethylbenzyl ammonium salt, dialkyldimethyl ammonium salt, or heteroaromatic ammonium salt wherein the anion portion of the molecule is a large, high-molecular weight (MW) organic ion. Some non-limiting examples of polysubstituted quaternary ammonium salts include alkyldimethyl benzyl ammonium saccharinate, commercially available as Onyxide 3300 from Stepan Company (Northfield, Ill.); and dimethylethylbenzyl ammonium cyclohexylsulfamate, commercially available as Onyxide 172 from Stepan Company (Northfield, Ill.).

Bis-quaternary ammonium salts contain two symmetric quaternary ammonium moieties having the general formula:

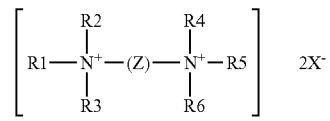

Here the R groups may be long or short chain alkyl, a benzyl radical or provided by an aromatic system. Z is a carbon-hydrogen chain attached to each quaternary nitrogen. Some non-limiting examples of bis-quaternary ammonium salts include 1,10-bis(2-methyl-4-aminoquinolinium chloride)-decane; and 1,6-bis [1-methyl-3-(2,2,6-trimethyl cyclohexyl)-propyldimethylammonium chloride] hexane or triclobisonium chloride.

A wide variety of different types of polymeric quaternary ammonium salts are known. Some non-limiting examples of polymeric quaternary ammonium salts include the following:

A. Ionenes having the following structure:

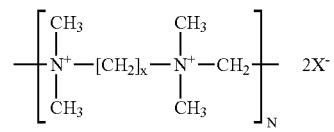

B. Poly[oxyethylene(dimethyliminio)ethylene(dimethyliminio)ethylene dichloride], having the following structure:

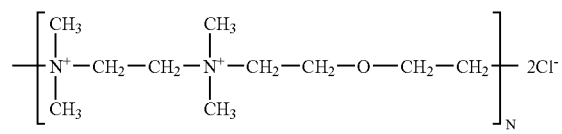

C. Polyquaternium 2 CTFA, having the following structure and are commercially available as Mirapol-A15 from Rhodia Inc. (Lawrenceville, Ga.):

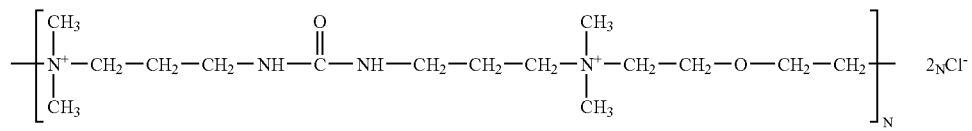

D. Polyquaternium 1 CTFA, having the following structure:

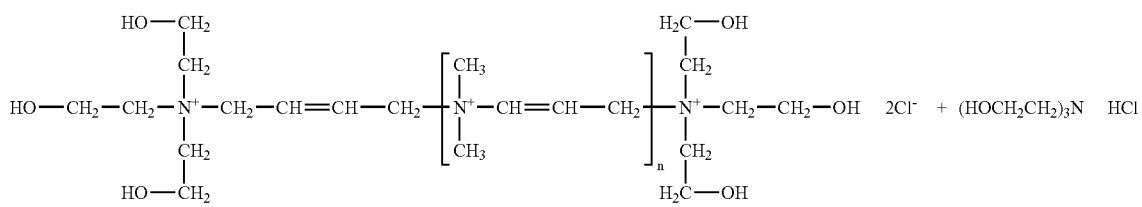

The long-chain alkyl R groups in the previously described quats have from about 8 carbons to about 18 carbons, from about 10 to about 18 carbons, and from about 12 to about 16 carbons. Such quats are both soluble and good antimicrobial agents.

The term "anionic counterion" includes any ion that can form a salt with quaternary ammonium. Examples of suitable counterions include halides such as chlorides and bromides, propionates, methosulphates, saccharinates, ethosulphates, hydroxides, acetates, phosphates, and nitrates. Preferably, the anionic counterion is chloride.

The quaternary ammonium compound is preferably selected from the following classes: monoalkyldimethylbenzyl ammonium salts, dialkyldimethyl ammonium salts, polysubstituted quaternary ammonium salts, and bis-quaternary ammonium salts, with the monoalkyldimethylbenzyl ammonium salts being the most preferred.

In a preferred embodiment, the quaternary ammonium compound is considered a food additive. The quaternary ammonium compound is preferably benzalkonium chloride or benzethonium chloride.

The composition of the invention may include one quaternary ammonium compound, or a mixture of two or more quaternary ammonium compounds. The composition of the invention can include a quaternary ammonium compound in an amount effective for providing antimicrobial activity to the composition of the invention. A quaternary ammonium compound can be present in a use composition in an amount up to about 5 wt. %, preferably from about 0.01 to about 3 wt. %, from about 0.05 to about 2 wt. %, and from about 0.1 to about 0.5 wt. %.

Thickener

The composition preferably includes a thickener so that the composition is a viscous liquid, gel, or semisolid that can be easily applied to and rubbed on the skin.

Suitable thickeners may be organic or inorganic in nature. The thickener may thicken the composition by either thickening the aqueous portions of the composition, or by thickening the non-aqueous portions of the composition. In a preferred embodiment, the composition is not an emulsion.

Thickeners can be divided into organic and inorganic thickeners. Of the organic thickeners there are (1) cellulosic thickeners and their derivatives, (2) natural gums, (3) acrylates, (4) starches, (5) stearates, and (6) fatty acid alcohols. Of the inorganic thickeners there are (7) clays, and (8) salts. Some non-limiting examples of cellulosic thickeners include carboxymethyl hydroxyethylcellulose, cellulose, hydroxybutyl methylcellulose, hydroxyethylcellulose, hydroxypropylcellulose, hydroxypropyl methyl cellulose, methylcellulose, microcrystalline cellulose, sodium cellulose sulfate, and the like. Some non-limiting examples of natural gums include acacia, calcium carrageenan, guar, gelatin, guar gum, hydroxypropyl guar, karaya gum, kelp, locust bean gum, pectin, sodium carrageenan, tragacanth gum, xanthan gum, and the like. Some non-limiting examples of acrylates include potassium aluminum polyacrylate, sodium acrylate/vinyl alcohol copolymer, sodium polymethacrylate, and the like. Some non-limiting examples of starches include oat flour, potato starch, wheat flour, wheat starch, and the like. Some non-limiting examples of stearates include methoxy PEG-22/dodecyl glycol copolymer, PEG-2M, PEG-5M, and the like. Some non-limiting examples of fatty acid alcohols include caprylic alcohol, cetearyl alcohol, lauryl alcohol, oleyl alcohol, palm kernel alcohol, and the like. Some non-limiting examples of clays include bentonite, magnesium aluminum silicate, magnesium trisilicate, stearalkonium bentonite, tromethamine magnesium aluminum silicate, and the like. Some non-limiting examples of salts include calcium chloride, sodium chloride, sodium sulfate, ammonium chloride, and the like.

Some non-limiting examples of thickeners that thicken the non-aqueous portions of the composition include waxes such as candelilla wax, carnauba wax, beeswax, and the like, oils, vegetable oils and animal oils, and the like.

The composition may contain one thickener or a mixture of two or more thickeners. Preferred thickeners do not adversely react with the quaternary ammonium compounds of the invention to decrease the antimicrobial activity of the quaternary ammonium compound or otherwise render the composition of the invention ineffective. It is understood that a person skilled in the art will know how to select an appropriate thickener and control any adverse reactions through formulating. In a preferred embodiment, the thickener is considered a food additive. There are many examples of suitable food additive thickeners. The preferred thickeners for the compositions of the invention are polyacrylic acid copolymer, commercially available as Carbopol 1342 from BF Goodrich (Brecksville, Ohio), and hydroxypropyl methylcellulose, commercially available as Methocel 40–101 from The Dow Chemical Company (Midland, Mich.).

The amount of thickener present in the composition depends on the desired viscosity of the composition. The composition preferably has a viscosity from about 100 to about 15,000 centipoise, from about 150 to about 10,000 centipoise, and from about 200 to about 5,000 centipoise as determined using a Brookfield DV-II+rotational viscometer using spindle # 21 @ 20 rpm @ 70° F. Accordingly, to achieve the preferred viscosities, the thickener may be present in the composition in an amount from about 0.001 wt. % to about 5 wt. % of the total composition, from about 0.01 wt. % to about 3 wt. %, and from about 0.05 wt. % to about 2 wt. % of the total composition.

Solvent

The composition preferably includes a solvent. Suitable solvents include water, alcohols, esters, ethers, glycols, glycol ethers, aldehydes, glycerin, and mixtures thereof. Some non-limiting examples of suitable alcohols include ethanol, propanols, butanols, and mixtures thereof. If an alcohol is selected as the solvent, the alcohol preferably enhances the drying time of the sanitizer composition. The drying time is preferably under one minute, under 30 seconds, and 15 seconds. Alcohols with longer carbon chains take more time to dry than alcohols with shorter carbon chains. Therefore, the carbon chain is preferably from 2 to 5 carbons long, from 2 to 4 carbons long, and from 2 to 3 carbons long.

Additional suitable solvents include ethylene glycol, propylene glycol, diethylene glycol, dipropylene glycol, triethylene glycol, tripropylene glycol, and hexylene glycol.

In a preferred embodiment, the solvent is considered a food additive. Suitable food additive solvents include water and ethanol.

The compositions of the invention may include a mixture of two or more solvents. Suitable solvents will provide the benefits of a solvent, such as dissolving the other composition components, without rendering the quaternary ammonium compound ineffective. In the compositions of the invention, the solvent is preferably water, ethanol sold under the trade name Ethanol SDA-3C, available from The Dow Chemical Company (Midland, Mich.) or isopropanol, available from Union Carbide Corp. (Danbury, Conn.).

The solvent can be present in a use composition in an amount up to about 99.9 wt. %, preferably from about 25 to about 99, from about 50 to about 95, and from about 75 to about 95.

Other Ingredients

Other active ingredients may optionally be used to improve the effectiveness of the sanitizer composition. Some non-limiting examples of such additional active ingredients can include: pH adjusters, skin conditioners, drying time enhancers, dyes, fragrances, and the like, and other ingredients useful in imparting a desired characteristic or functionality in the sanitizer composition. The following describes some examples of such ingredients. These ingredients can be used in any amount to achieve the desired results.

pH Adjusters

The composition may optionally include a pH adjuster. A pH adjuster may be included to adjust the pH to activate the thickener or to provide a pH that is compatible with the pH of the user's skin. The pH is preferably in the range from 2 to 11, from 5 to 10, and from 6 to 9. Any acidic or alkaline agent that provides the desired pH may be used as a pH adjuster.

The pH adjusters can generally be divided into four groups: (1) organic acids, (2) organic bases, (3) inorganic acids, and (4) inorganic bases. Some non-limiting examples of organic acids include acetic acid, benzoic acid, ascorbic acid, azelaic acid, citric acid, fumaric acid, glucuronic acid, glycolic acid, ketoglutaric acid, lactic acid, maleic acid, malic acid, malonic acid, oxalic acid, propionic acid, quinic acid, sebacic acid, succinic acid, tartaric acid, and the like. Some non-limiting examples of organic bases include ammonium bicarbonate, ammonium carbamate, ammonium carbonate, ammonium glycolate, diethanolamine, diethanolamine bisulfate, diisopropanolamine, diisopropylamine, dimethyl MEA, dioleoyl edetolmonium methosulfate, dipropylenetriamine, ethanolamine, isopropylamine, morpholine, potassium bicarbonate, potassium carbonate, sodium bicarbonate, and the like. Some non-limiting examples of inorganic acids include hydrochloric acid, sulfuric acid, phosphoric acid, and the like. Some non-limiting examples of inorganic bases include calcium dihydrogen phosphate, dipotassium phosphate, disodium phosphate, disodium pyrophosphate, magnesium carbonate, potassium hydroxide, sodium hydroxide, and the like.

Preferable pH adjusters include triethanolamine and citric acid.

In a preferred embodiment, the pH adjuster is considered a food additive. Suitable food additive pH adjusters include citric acid and triethanolamine.

A person skilled in the art will recognize the different strengths of acids and bases and formulate accordingly. In an embodiment, the pH adjuster can be present in a use composition in an amount up to about 10 wt. %, preferably from about 0.01 to about 8 wt. %, from about 0.1 to about 5 wt. %, and from about 0.2 to about 2 wt. %.

Skin Conditioners

The composition may optionally include an emollient, humectant, occlusive agent, or other moisturizer to provide moisturizing, skin softening, or anti-irritation benefits. Any composition that provides these benefits may be used with this invention. Some non-limiting examples of emollients include cetyl myristate, glyceryl dioleate, methyl laurate, PPG-9 laurate, soy stearyl, octyl palmitate, PPG-5 lanoate, lanolin, propylene glycol, glycerine, fatty acids, natural oils such as almond, mineral, canola, sesame, soybean, wheat germ, corn, peanut, and olive, isopropyl myristate, myristyl alcohol, aloe vera, hydrolyzed silk protein, Vitamin E, stearyl alcohol, isopropyl palmitate, sorbitol, amino acid complexes, and polyethylene glycol. Some non-limiting examples of humectants include agarose, arginine PCA, fructose, glucose, glutamic acid, glycerine, honey, lactose, maltose, propylene glycol, sorbitol and mixtures thereof. Some non-limiting examples of occlusive agents include avocado oil, balm mint oil, butter, canola oil, cod liver oil, corn oil, methicone, mineral oil, olive oil, phenyl trimethicone, trimyristin, stearyl stearate, synthetic wax, or mixtures thereof. Finally, some non-limiting examples of other moisturizers include aloe, cholesterol, cystine, keratin, lecithin, egg yolk, glycine, PPG-12, retinol, salicylic acid, orotic acid, vegetable oil, and mixtures thereof.

In the preferred embodiment, the skin conditioner is considered a food additive. Examples of suitable food additive skin conditioners include glycerine, propylene glycol, and myristyl alcohol.

The skin conditioner is preferably propylene glycol, glycerine, myristyl alcohol, isopropyl myristate, Vitamine E, or Lanolin. A person skilled in the art will recognize the different strengths of different skin conditioners and formulate accordingly. In an embodiment, the skin conditioner can be present in a use composition in an amount up to about 10 wt. %, preferably from about 0.01 to about 5 wt. %, from about 0.1 to about 5 wt. %, and from about 0.1 to about 3 wt. %.

Drying Time Enhancers

The composition may optionally include a drying time enhancer to aid in the evaporation of the product off of the user's skin. The drying time enhancer is preferably water soluble. Examples of suitable drying time enhancers include ethanol, propanols, butanols, mineral spirits, and mixtures thereof.

In a preferred embodiment, the drying time enhancer is considered a food additive. Examples of suitable food additive drying time enhancers include ethanol.

The drying time enhancer can be present in a use composition in an amount up to about 60 wt. %, preferably from about 1 to about 30 wt. %, and from about 5 to about 25 wt. %.

Dyes

The composition may optionally include a dye. Examples of dyes include any water soluble or product soluble dye, any FD&C or D&C approved dye, Blue 1, FD&C Yellow 5, Resorcin Brown, Red 40, Direct Blue 86 (Miles), Fastusol Blue (Mobay Chemical Corp), Acid Orange 7 (American Cyanamid), Basic Violet 10 (Sandoz), Acid Yellow 23 (GAF), Acid Yellow 17 (Sigma Chemical), Sap Green (Keyston Analine and Chemical), Metanil Yellow (Keyston Analine and Chemical), Acid Blue 9 (Hilton Davis), Sandolan Blue/Acid Blue 182 (Sandoz), Hisol Fast Red (Capitol Color and Chemical), Fluorescein (Capitol Color and Chemical), Acid Green 25 (Ciba-Geigy), and the like. The dye is preferably a water soluble dye. Also, the dye is preferably a FD&C or D&C approved dye.

In a preferred embodiment, the dye is considered a food additive. Examples of suitable food additive dyes include FD&C dyes.

The dye can be present in a use composition in an amount up to about 0.5 wt. %, preferably from about 0.00001 to about 0.1 wt. %, from about 0.0001 to about 0.01 wt. %, and from about 0.0001 to about 0.0005 wt. %.

Fragrance

The composition may optionally include a fragrance. Examples of possible fragrances include natural oils or naturally derived materials, and synthetic fragrances such as hydrocarbons, alcohols, aldehydes, ketones, esters, lactones, ethers, nitriles, and polyfunctionals. Non-limiting examples of natural oils include the following: *Abies sibirica* oil, *Amyri balsamifera* oil, balm mint (*Melissa officinalis*) oil, basil (*Ocimum basilicum*) oil, bay (*Pimento acris*) oil, bee balm (*Monarda didyma*) oil, bergamot (*Citrus aurantium bergamia*) oil, birch (*Betula alba*) oil, bitter almond (*Prunus amygdalus amara*) oil, bitter cherry (*Prunus cerasus*) oil, bitter orange (*Citrus aurantium amara*) oil, cabbage rose (*Rosa centifolia*) oil, *Calendula officinalis* oil, California nutmeg (*Torreya califonica*) oil, caraway (*Carum carvi*) oil, caraway (*Carum carvi*) seed oil, cardamom (*Elettaria cardamomum*) oil, cedarwood (*Cedrus atlantica*) oil, *Chamaecyparis obtuse* oil, chamomile (*Anthemis nobilis*) oil, cinnamon (*Cinnamomum cassia*) oil, citronella (*Cymbopogon nardus*) oil, clary (*Salvia sclarea*) oil, clove (*Eugenia caryophyllus*) oil, cloveleaf (*Eufenia caryophyllus*) oil, *Cyperus esculentus* oil, cypress (*Cupressus sempervirens*) oil, *Eucalyptus citriodora* oil, eucalyptus globules oil, fennel (*Foeniculum vulgare*) oil, galbanum (*Ferula galbaniflua*) oil, *Gardenia florida* oil, geranium maculatum oil, ginger (*Zingiber officinale*) oil, grapefruit (*Citrus grandis*) oil, hazel (*Corylus avellana*) nut oil, hops (*Humulus lupulus*) oil, *Hyptis suaveolens* oil, indigo bush (*Dalea spinosa*) oil, jasmine (*Jasminum officinale*) oil, *Juniperus communis* oil, *Juniperus oxycedrus* tar, *Juniperus virginiana* oil, kiwi (*Actinidia chinensis*) water, labdanum (*Cistus labdaniferus*) oil, laurel (*Laurus nobilis*) oil, lavandin (*Lavandula hybrida*) oil, lavender (*Lavandula angustifolia*) oil, lavender (*Lavandula angustifolia*) water, lemon (*Citrus medica limonum*) oil, lemongrass (*Cymbopogon schoenanthus*) oil, *Leptospermum scoparium* oil, lime (*Citrus aurantifolia*) oil, linden (*Tilia cordata*) oil, linden (*Tilia cordata*) water, *Litsea cubeba* oil, lovage (*Levisticum officinale*) oil, mandarin orange (*Citrus nobilis*) oil, massoy bark oil, matricaria (*Chamomilla recutita*) oil, moraccan chamomile oil, mugwort (*Artemisia princeps*) water, musk rose (*Rosa moschata*) oil, myrica gale extract, myrrh (*Commiphora myrrha*) oil, *Myrrhis odorata* extract, myrtle (*Myrtus communis*) oil, Norway spruce (*Picea excelsa*) oil, nutmeg (*Myristica fragrans*) oil, *Olax dissitiflora* oil, opoponax oil, orange (*Citrus aurantium dulcis*) flower oil, orange (*Citrus aurantium dulcis*) oil, orange (*Citrus aurantium dulcis*) water, palmarosa (*Cymbopogon martini*) oil, parsley (*Carum petroselinum*) seed oil, patchouli (*Pogostemon cablin*) oil, *Pelagonium graveolens* oil, pennyroyal (*Mentha pulegium*) oil, peppermint (*Menthe piperita*) oil, peppermint (*Menthe peperita*) water, pine (*Pinus palustris*) oil, pine (*Pinus palustris*) oil, pine (*Pinus palustris*) tar oil, pine (*Pinus pumilio*) oil, pine (*Pinus suulvestris*) cone oil, rosemary (*Rosmarinus officinalis*) oil, rose oil, rose (*Rosa damascena*) extract, rose (*Rosa multiflora*) extract, rosewood (*Aniba rosaeodora*) extract, rue (*Ruta graveolens*) oil, sage (*Salvia officinalis*) oil, sage (*Salvia officinalis*) water, *Sambucus nigra* oil, sandalwood (*Santalum album*) oil, *Sassafras officinale* oil, silver fir (*Abies pectinata*) oil, *Sisymbrium irio* oil, spearmint (*Menthe viridis*) oil, sweet marjoram (*Origanum majorana*) oil, sweet violet (*Viola odorata*) oil, tar oil, tea tree (*Melaleuca alternifolia*) oil, *Thuja occidentalis* oil, thyme (*Thymus vulgaris*) oil, wild mint (*Menthe arvensis*) oil, wild mint (*Menthe arvensis*) powder, *Ximenia americana* oil, yarrow (*Achillea millefolium*) oil, ylang ylang (*Cananga odorata*) oil. Some non-limiting examples of synthetic hydrocarbon fragrances include caryophyllene, β-farnesene, limonene, α-pinene, and β-pinene. Some non-limiting examples of synthetic alcohol fragrances include Bacdanol, citronellol, linalool, phenethyl alcohol, and α-terpineol (R=H). Some non-limiting examples of synthetic aldehyde fragrances include 2-methyl undecanal, citral, hexyl cinnamic aldehyde, Isocycolcitral, Lilial, and 10-undecenal. Some non-limiting examples of synthetic ketone fragrances include Cashmeran, α-ionone, Isocyclemone E, Koavone, muscone, and Tonalide. Some non-limiting examples of synethetic ester fragrances include benzyl acetate, 4-t-butylcyclohexyl acetate (cis and trans), cedryl acetate, Cyclacet, isobornyl acetate, and α-terpinyl acetate (R=acetyl). Some non-limiting examples of synthetic lactone fragrances include coumarin, jasmine lactone, muskalactone, and peach aldehyde. Some non-limiting examples of synthetic ether fragrances include Ambroxan, Anther, and Galaxolide. Some non-limiting examples of synthetic nitrile fragrances include cinnamonitrile and gernonitrile. Finally, some non-limiting examples of synthetic polyfunctional fragrances include amyl salicylate, isoeugenol, Hedione, heliotropine, Lyral, and vanillin.

The composition may include a mixture of fragrances including a mixture of natural and synthetic fragrances. Suitable fragrances will provide the benefits of a fragrance without rendering the quaternary ammonium compound ineffective.

In a preferred embodiment, the fragrance is considered a food additive. Examples of suitable food additive fragrances include citrus, anise, jasmine, lavender, lime, lemon, rose, and vanilla.

The fragrance can be present in a use composition in an amount up to about 5 wt. %, preferably from about 0.01 to about 3 wt. %, from about 0.05 to about 1 wt. %, and from about 0.1 to about 0.2 wt. %.

Thickened Quaternary Ammonium Compound Sanitizer Composition and Use

The compositions of the invention may be used by any user desiring to sanitize their hands. The compositions of the invention are especially useful for users in industries where proper hand care is especially important, such as the hospital, health care, and food and beverage industries.

The composition of the invention may be used either by itself or as part of a hand sanitizing program. When used by itself, the composition of the invention is applied to the user's hands, preferably in quantity of from about 0.1 to about 1 mLs, from about 0.5 to about 8 mLs, and from about 1 to about 5 mLs, and rubbed on the hands until substantially all of the product is either evaporated or absorbed. The composition is preferably rubbed on the user's hands from about 5 seconds to about 60 seconds. This process may be repeated as often as necessary in order to maintain proper hand sanitation. When used as part of a hand sanitizing program, the user first washes their hands with a cleansing wash using water and a skin cleansing composition such as CONQUEST™ Antibacterial Hand Soap commercially available from Ecolab Inc., or comparable skin cleansing composition. The cleaning wash step preferably lasts from about 30 seconds to about 60 seconds. The composition of the invention is then applied to the user's hands, preferably in an amount the size of about 1 to about 5 mLs, and rubbed on the hands until substantially all of the product is either evaporated or absorbed. The composition of the invention is preferably rubbed on the user's hands from about 5 seconds to 60 seconds. This two step process may be repeated as often as necessary in order to maintain proper hand sanitation.

While this invention may be used as a hand sanitizer, it is understood that this chemistry has other applications such as a hard surface sanitizer, a food sanitizer, and a teat dip.

For a more complete understanding of the invention, the following examples are given to illustrate some embodiments. These examples and experiments are to be understood as illustrative and not limiting. All parts are by weight, except where it is contrarily indicated.

EXAMPLES

The following chart provides a brief explanation of certain chemical components used in the following examples:

TABLE 1

Trade Names and Corresponding Descriptions of Some Chemicals Used in the Examples

| Trademark/Chemical Name | Description | Provider |
|---|---|---|
| | Propylene Glycol | Dow Chemical |
| LonzaGuard | Benzethonium Chloride | Lonza |
| FD&C Red # 40 | Dye | Pylam |
| Methocel 40-101 | Hydroxpropyl methylcellulose | Dow Chemical |
| TEA | Triethanolamine | Dow Chemical |
| Ethanol SDA-3 | Ethanol | Dow Chemical |
| IPA | Isopropanol | Ashland Chemical |
| Carbopol 1342 | Acrylic Polymer | BF Goodrich |
| Barquat MB-80 | 80% Solution of Quaternary Ammonium Compound | Lonza |

Example 1

Example 1 tested the minimum viscosity level required to maintain acceptable containment when using the thickened quaternary ammonium compound sanitizer composition. Containment refers to the product remaining on a user's hands and not running off. A panel test was used to determine acceptable containment because containment is a subjective test. Panel test participants were selected and asked to evaluate both containment and spreading characteristics of seven different samples of the thickened quaternary ammonium sanitizer composition. Table 2 shows the seven formulas that were tested. The mix order for the formulas was as follows: (1) water; (2) isopropanol; (3) Carbopol; (4) propylene glycol; (5) Red #40; (6) triethanolamine; and (7) Barquat MB-80.

TABLE 2

Formulas Used in Viscosity Assessment

| | Formula | | | | | |
|---|---|---|---|---|---|---|
| | 1 | 2 | 3 | 4 | 5 | 6 |
| | Viscosity (cPs) | | | | | |
| Raw Material | 0 | 200 | 300 | 425 | 510 | 1080 |
| Water | 91.3599 | 90.5599 | 90.6199 | 90.6899 | 90.6599 | 90.7299 |
| Isopropanol | 7.0000 | 7.0000 | 7.0000 | 7.0000 | 7.0000 | 7.0000 |
| Carbopol 1342 | 0 | 0.1900 | 0.1900 | 0.1900 | 0.1900 | 0.1900 |
| Propylene Glycol | 1.4800 | 1.5000 | 1.5000 | 1.5000 | 1.5000 | 1.5000 |
| Red #40 | 0.0001 | 0.0001 | 0.0001 | 0.0001 | 0.0001 | 0.0001 |
| TEA, 99% | 0 | 0.4000 | 0.4000 | 0.4000 | 0.4000 | 0.4000 |
| Barquat MB-80 | 0.1600 | 0.3500 | 0.2900 | 0.2200 | 0.2500 | 0.1800 |
| Total | 100 wt. % | 100 wt. % | 100 wt. % | 100 wt. % | 100 wt. % | 100 wt. % |

These samples ranged from 0 to 1080 cPs in viscosity as determined using a Brookfield DV-II+rotational viscometer using spindle # 21 @ 20 rpm @ 70° F. Each sample of product was placed into a jar and labeled 1–6 to allow identification by the panelists. Each participant was tested individually and given a brief overview of the test procedure, however, details about specific viscosities or other panelists responses were withheld to eliminate any bias. Each person was instructed to take approximately 0.5 g of sample using a disposable pipette and place it into their palm. They were asked to evaluate the sample for containment and spreading characteristics. Each sample was rubbed into the skin completely and a waiting period of 1–2 minutes was used to allow the hands adequate time to dry before moving on to the next sample. After the testing was complete, each panelist was asked to provide feedback on the samples regarding whether the sample containment and spreading characteristics were adequate. The panelists were asked to characterize the sample as (1) too thin; (2) OK; (3) good; (4) best; and (5) too thick. Table 3 shows the summary of the panelist responses.

TABLE 3

Summary of Panelist Responses in Viscosity Assessment

| Panelist | Formula 1 0 cPs | Formula 2 200 cPs | Formula 3 300 cPs | Formula 4 425 cPs | Formula 5 510 cPs | Formula 6 1080 cPs |
|---|---|---|---|---|---|---|
| A | Too Thin | Too Thin | Too Thin | Good | Good | Good |
| B | OK | OK | OK | Good | Good | Good |

TABLE 3-continued

Summary of Panelist Responses in Viscosity Assessment

| Panelist | Formula 1 0 cPs | Formula 2 200 cPs | Formula 3 300 cPs | Formula 4 425 cPs | Formula 5 510 cPs | Formula 6 1080 cPs |
|---|---|---|---|---|---|---|
| C | Too Thin | Too Thin | Too Thin | Good | Best | Good |
| D | Too Thin | OK | OK | Good | Good | Good |
| E | Too Thin | OK | OK | Good | Good | Good |
| F | Too Thin | Too Thin | Too Thin | Too Thin | Best | Good |
| G | Too Thin | OK | Good | Best | Too Thick | Too Thick |
| H | Too Thin | Too Thin | Too Thin | Good | Best | Too Thick |
| I | Too Thin | Too Thin | Good | Good | Good | Too Thick |
| J | Too Thin | Too Thin | Good | Best | Best | Good |
| K | Too Thin | Too Thin | Good | Best | Best | Good |
| L | Too Thin | Good | Good | Good | Good | Good |
| M | Too Thin | OK | Good | Good | Good | Good |
| # Accepted | 1 | 6 | 9 | 12 | 12 | 10 |
| % Accepted | 8% | 46% | 69% | 92% | 92% | 77% |

Responses of OK, Good, or Best were considered acceptable responses whereas responses of Too Thin, or Too Thick were considered unacceptable responses. The highest preference levels occurred between 300 cPs and 1080 cPs (Formulas 3, 4, 5, and 6 with acceptance levels of 69%, 92%, 92%, and 77% respectively. The optimum preference for maximizing viscosity, containment, and spreading characteristics occurred between 400–500 cPs (Formulas 4, and 5 with acceptance levels of 92% each). A majority of panelists comments centered around the lack of containment of the thinner product and the change in consistency of the thicker version. They felt that the lotion type feel of the mid-viscosity samples best fit their conception of this type of hand sanitizing product.

Example 2

Example 2 compared the bactericidal efficacy of the thickened quaternary ammonium compound sanitizer composition (Formula 7) to that of a known concentration of chlorine. Table 4 shows the composition of Formula 7 and the chlorine standard. The mix order for Formula 7 is as follows: (1) water; (2) propylene glycol; (3) LonzaGuard; (4) FD&C Red #40; (5) Methocel; (6) Triethanolamine; and (7) Ethanol. Formula 7 and the chlorine standard were tested against *Staphylococcus aureus*, ATCC # 6538 and *Salmonella typhi*, ATCC # 6539. The chlorine standard was prepared by adding 0.1 ml of a 5% NaOCl stock solution (refrigerated Clorox® bleach) to 100 ml of sterile phosphate buffer solution to create a 50–55 ppm available chlorine concentration.

For the chlorine standard test, 0.05 ml of the test culture was added to a test tube with 50 ppm available chlorine. The test tube was placed in a 20° C. water bath. After 1 minute, the solution was transferred to test tube 1 with 10 ml of Fluid Thioglycollate medium (commercially available from Becton Dickinson (Sparks, Md.)). These steps were repeated for nine test tubes.

For Formula 7, the same series of test tubes used for the available chlorine test was used to test the quaternary ammonium compound sanitizer composition. 0.05 ml of test culture was added to Formula 7. The test tube was placed in a 20° C. water bath. After 1 minute, the solution was transferred to a test tube with 10 ml of Letheen broth in place of the Fluid Thioglycollate medium.

TABLE 4

Quaternary Ammonium Formula and Chlorine Standard

| Formula 7 | Chlorine Standard |
|---|---|
| 20% Ethanol SDA-3 | 0.1 ml of 5% NaOCl Stock |
| 78% Water | 100 ml Sterile Phosphate Buffer Solution |
| 1% Propylene Glycol | |
| 0.2% LonzaGuard | |
| 0.0001% FD&C Red #40 | |
| 0.5% Methocel 40-101 | |
| 0.01% Triethanolamine | |

The formulas in Table 4 were tested with *Staphylococcus aureus*, ATCC # 6538 and *Salmonella typhi*, ATCC # 6539. Table 5 shows the results tests. A "+" sign means that the test tube had bacteria growth. A "−" sign means that the test tube did not have bacteria growth.

TABLE 5

Antimicrobial Efficacy of a Thickened Quaternary Ammonium Composition vs. Chlorine Standard

| Germicide | Available Chlorine | Organism | Test Tube | | | | | | | | | |
|---|---|---|---|---|---|---|---|---|---|---|---|---|
| | | | 1 | 2 | 3 | 4 | 5 | 6 | 7 | 8 | 9 | 10 |
| Formula 7 | | *S. aureus* | − | − | − | − | − | − | − | − | − | − |
| | | *S. typhi* | − | − | − | − | − | − | − | − | − | − |
| NaOCl | 50 ppm | *S. aureus* | − | − | + | + | + | + | + | + | + | + |
| | | *S. typhi* | − | − | + | + | + | + | + | + | + | + |

(+) = growth;
(−) = no growth

According to the USDA List of Proprietary Substances and Nonfood Compounds last published in 1998, a handwashing and sanitizing composition should possess efficacy equivalent to 50 ppm chlorine. Equivalency is met when the sample tubes have an absence of growth in as many tubes as the chlorine standard. The chlorine standard had growth in tubes 3–10 while Formula 7 did not have any growth in tubes 1–10. Therefore, Example 2 demonstrates that the quaternary ammonium compositions of the invention are more efficacious against bacteria than the chlorine standard.

Example 3

Example 3 tested the minimum level of quaternary ammonium compound necessary for the growth inhibition of the test organism. Formula 7 from Table 4 was tested against *Staphylococcus aureus* (ATCC # 6538); *Salmonella typhi* (ATCC # 6539); *Escherichia coli* (ATCC # 11229); *Salmonella enteritidis* (ATCC # 13076); *Salmonella choleraesuis* (ATCC # 10708); *Listeria monocytogenes* (ATCC # 7644); *Pseudomonas stutzeri* (ATCC # 17588); *Shigella sonnei* (ATCC # 11060); *Klebsiella pneumoniae* (ATCC # 10031); and *Salmonella typhimurium* (ATCC # 13311).

The test substances were prepared by transferring the test organisms from stock culture to the appropriate culture media. The culture media was either nutrient broth, or tryptic soy broth. The test organisms were incubated for 24–48 hours at 36° C. The test organisms were consecutively transferred from 4 to 15 times. The turbidity of the culture was adjusted to be visually comparable to a standard (0.5 McFarland standard) by adding sterile broth to the culture. Resulting cultures with a visual turbidity similar to the standard contained approximately $10^8$ cfu/ml. The cultures were then diluted in sterile broth to prepare a test system suspension having $10^7$ cfu/ml.

Ten milliliters of Formula 7 were then added to a 2× concentration of Mueller Hinton broth, resulting in 20 ml of a 1:2 dilution of Formula 7. The 1:2 dilution was then further diluted in 10 ml of 1× concentration of Mueller Hinton broth to prepare a series of dilutions ranging from 1:2 to 1:1024. These dilutions were then inoculated with 0.1 ml of the test system suspension organisms to obtain approximately $10^5$ cfu/ml of the organism in the test tube. The tubes were incubated at 36° C. for 24–48 hours and then examined for growth (turbidity). The Minimum Inhibitory Concentration (MIC) was then recorded. The MIC is the minimum level of quaternary ammonium compound necessary for the complete inhibition of growth of the test system. The MIC recorded was the lowest concentration in which no turbidity was visually detected in the tube.

TABLE 6

Minimum Inhibitory Concentration of Quaternary Ammonium Formula

| Test Organism | MIC |
| --- | --- |
| *Staphylococcus aureus* (ATCC # 6538) | 1:1024 |
| *Salmonella typhi* (ATCC # 6539) | 1:64 |
| *Escherichia coli* (ATCC # 11229) | 1:32 |
| *Salmonella enteritidis* (ATCC # 13076) | 1:128 |
| *Salmonella choleraesuis* (ATCC # 10708) | 1:32 |
| *Listeria monocytogenes* (ATCC # 7644) | 1:256 |
| *Pseudomonas stutzeri* (ATCC # 17588) | 1:64 |
| *Shigella sonnei* (ATCC # 11060) | 1:128 |
| *Klebsiella pneumoniae* (ATCC # 10031) | 1:256 |
| *Salmonella typhimurium* (ATCC # 13311) | 1:64 |

Example 4

Example 4 tested the ability of Formula 7 to kill *E. coli* (ATCC #11229), *K. pneumoniae* (ATCC #10031), *S. typhi* (ATCC #6539), *S. aureus* (ATCC #6538), and *L. monocytogenes* (ATCC #7644) at 1 and 5 minute contact times.

Test organisms were suspended in phosphate buffer at a concentration of $10^8$. 0.05 ml of the suspension was added to 10 ml of Formula 7. At one minute contact time, one milliliter of the mixture was added to 9 ml of Modified Letheen Broth and plated. Plating was repeated after five minutes of contact time. Formula 7 was tested against a phosphate buffer control. All tests were done in duplicate and the results provided as an average of two tests. Table 7 shows the results.

TABLE 7

Time Kill Study Results

| | Time | |
| --- | --- | --- |
| Test Organism | 1 Min. | 5 Mins. |
| *E. coli* | >99.9% | >99.9% |
| *K. pneumoniae* | >99.9% | >99.9% |
| *S. typhi* | >99.9% | >99.9% |
| *S. aureus* | >99.9% | >99.9% |
| *L. monocytogenes* | >99.9% | >99.9% |

Table 7 shows that Formula 7 kills more than 99.9% (3 logs) of the microorganisms tested at 1 minute and 5 minutes.

Example 5

Example 5 tested the ability of the composition of the invention to reduce *E. coli* when used in conjunction with a cleansing step versus the cleaning step alone without the composition of the invention. Fifteen subjects completed this study by applying the cleaning step plus the composition of the invention. For this study, the subjects' hands were first artificially contaminated with 4.5 ml of an *E. coli* (ATCC #11229) suspension (minimum of $10^8$ organisms per ml) where the suspension was added to the subjects cupped hands in 1.5 ml increments. After each 1.5 ml increment, the suspension was rubbed over the hands for approximately 20 seconds, not going above the wrists, and allowed to air dry for approximately 30 seconds.

A baseline bacterial count was obtained by placing plastic bags (i.e. Glad Food Storage Bags) with 75 ml of stripping fluid (without neutralizer) over the subjects hands. The bag was secured to the subject and massaged for one minute. A sample of the fluid in the bag was taken within one minute of completing the massaging and diluted with phosphate buffer. The sample was then plated out and counted for *E. coli* colonies.

After the baseline count was taken, the subjects washed their hands for 20 seconds with IVORY® Skin Cleansing Liqui-Gel, followed by a 30 second to 2 minute treatment with Formula 5. After one treatment with the IVORY® Skin Cleansing Liqui-Gel and Formula 5, any remaining bacteria was collected off a subject's hands by placing plastic bags (i.e. Glad Food Storage Bags) with 75 ml of stripping fluid (without neutralizer) on the subject's hands, massaging, and then collecting a sample. The sample was diluted with phosphate buffer and then plated out and counted for *E. coli* colonies. The subjects hands were then artificially contaminated as before, and the process was repeated. Measurements were taken after the $1^{st}$, $3^{rd}$, $5^{th}$, $10^{th}$, and $11^{th}$ hand washings and the log reduction was calculated from the baseline measurement. Table 8 shows the log reduction from the baseline test of the fifteen subjects.

TABLE 8

Log Reduction of Two Step Cleaning Method

| Subject | Wash 1 | Wash 3 | Wash 5 | Wash 10 | Wash 11 |
|---|---|---|---|---|---|
| 1 | 3.0466 | 3.4640 | 3.3556 | 3.2285 | 2.6276 |
| 2 | 3.2481 | 3.1729 | 2.4715 | 2.5870 | 2.4990 |
| 3 | 2.8857 | 2.4585 | 1.7516 | 1.9155 | 1.4329 |
| 4 | 3.8376 | 3.0799 | 1.8504 | 2.4010 | 2.5265 |
| 5 | 2.3522 | 2.3943 | 2.6739 | 2.4609 | 2.1396 |
| 6 | 2.9098 | 3.3064 | 3.4598 | 3.2886 | 2.5190 |
| 7 | 2.0784 | 2.3249 | 2.2691 | 2.2229 | 2.0460 |
| 8 | 3.0614 | 2.6101 | 2.4457 | 2.7119 | 2.3752 |
| 9 | 2.8321 | 3.1202 | 3.3321 | 3.2879 | 2.7519 |
| 10 | 1.6914 | 1.6441 | 1.5697 | 1.6463 | 1.5393 |
| 11 | 3.0064 | 3.0073 | 2.7694 | 2.8513 | 2.5329 |
| 12 | 3.1264 | 3.4088 | 3.2771 | 3.2476 | 2.8753 |
| 13 | 1.4604 | 1.5641 | 1.5138 | 1.5412 | 1.3438 |
| 14 | 2.7852 | 2.9922 | 2.6916 | 2.7815 | 2.5387 |
| 15 | 2.2861 | 2.8653 | 2.8468 | 2.8339 | 2.1512 |
| Average | 2.7072 | 2.7609 | 2.5519 | 2.6004 | 2.2599 |
| Standard Deviation | 0.6243 | 0.5889 | 0.6572 | 0.5748 | 0.4804 |

Table 8 shows that the hand washing step together with the composition of the invention had a greater than 2 log reduction in *E. Coli* bacteria compared to the baseline measurements.

Example 6

Example 6 tested the level of irritation caused by the quaternary ammonium compound sanitizer composition of the invention. Formula 5 was used for this example. Twenty-five patients (four males and twenty-one females) participated in this study. Table 9 provides information on the participants.

TABLE 9

Irritation Study Demographics

| Age Range | Number of Subjects | Percent of Total |
|---|---|---|
| 18–27 | 1 | 4.0 |
| 28–37 | 8 | 32.0 |
| 38–47 | 6 | 24.0 |
| 48–57 | 2 | 8.0 |
| 58–67 | 0 | 0.0 |
| 68–77 | 3 | 12.0 |
| 78–87 | 5 | 20.0 |
| Totals | 25 | 100.0 |

Approximately 0.5 cc of Formula 5 was applied to Nu-Gauze™ (commercially available from Johnson & Johnson, Inc., New Brunswick, N.J.) and secured with 1 inch strips of Blenderm™ Tape (commercially available from 3M Corp., Maplewood, Minn.) to the patients. The dressings were removed daily except Saturday and Sunday and the skin was evaluated for a reaction. Product was then reapplied to fresh dressing for a total of 15 applications. A delayed challenge application was performed 14 days after the observation of the $15^{th}$ application. For the delayed challenge application, the product was reapplied for 24 hours and observations for this application were conducted at 48 and 72 hours after patch removal. Table 10 provides a summary of the testing schedule.

TABLE 10

Summary of Irritation Testing Schedule

| Day 1 | Initial application of test products and controls. |
|---|---|
| Days 1–18 | Daily application of test products except for Saturday and Sunday. |
| Day 21 | Final irritation observation day. |
| Day 35 | Delayed challenge product application. |
| Days 37–38 | Delayed challenge product application observation. |

The patients rated the level of irritancy on a scale of 0 to 3 with 0 being the least irritating and 3 being the most irritating. The results of the irritation study are provided in Table 11.

TABLE 11

Results of Irritation Study

| Participant | | Reaction by Grade | | | | | | | | | | | | | | | | | |
|---|---|---|---|---|---|---|---|---|---|---|---|---|---|---|---|---|---|---|---|
| | | Repetitive Irritation Test by Observation Day | | | | | | | | | | | | | | | | | |
| Sex | Age | 1 | 2 | 3 | 4 | 5 | 6 | 7 | 8 | 9 | 10 | 11 | 12 | 13 | 14 | 15 | Average Score | Delayed Challenge | |
| F | 33 | 0 | 0 | 0 | 0 | 0 | 0 | 0 | 0 | 0 | 0 | 0 | 0 | 0 | 0 | 0 | 0 | 0 | 0 |
| F | 52 | 0 | 0 | 0 | 0 | 0 | 0 | 0 | 0 | 0 | 0 | 0 | 0 | 0 | 0 | 1 | 0.07 | 0 | 0 |
| F | 74 | 0 | 0 | 0 | 0 | 0 | 0 | 0 | 0 | 0 | 0 | 0 | 0 | 0 | 0 | 0 | 0 | 0 | 0 |
| F | 72 | 0 | 0 | 0 | 0 | 0 | 0 | 0 | 0 | 0 | 0 | 0 | 0 | 0 | 0 | 0 | 0 | 0 | 0 |
| F | 29 | 0 | 0 | 0 | 0 | 0 | 0 | 0 | 0 | 0 | 0 | 0 | 0 | 0 | 0 | 0 | 0 | 0 | 0 |
| F | 48 | 0 | 0 | 0 | 0 | 0 | 0 | 0 | 0 | 0 | 0 | 0 | 0 | 0 | 0 | 0 | 0 | 0 | 0 |
| F | 38 | 0 | 0 | 0 | 0 | 0 | 0 | 0 | 0 | 0 | 0 | 0 | 0 | 0 | 0 | 0 | 0 | 0 | 0 |
| F | 33 | 0 | 0 | 0 | 0 | 0 | 0 | 0 | 0 | 0 | 0 | 0 | 0 | 0 | 0 | 0 | 0 | 0 | 0 |
| F | 47 | 0 | 0 | 0 | 0 | 1 | 1 | 1 | 0 | 0 | 0 | 0 | 0 | 0 | 0 | 0 | 0.2 | 0 | 0 |
| F | 42 | 0 | 0 | 0 | 0 | 0 | 0 | 0 | 0 | 1 | 0 | 0 | 0 | 0 | 0 | 0 | 0.07 | 0 | 0 |
| F | 68 | 0 | 0 | 0 | 0 | 1 | 0 | 0 | 0 | 0 | 0 | 0 | 0 | 0 | 0 | 0 | 0.07 | 0 | 0 |
| F | 43 | 0 | 0 | 0 | 0 | 0 | 0 | 0 | 0 | 0 | 0 | 0 | 0 | 0 | 0 | 0 | 0 | 0 | 0 |
| F | 38 | 0 | 0 | 0 | 0 | 0 | 0 | 0 | 0 | 0 | 0 | 0 | 0 | 0 | 0 | 0 | 0 | 0 | 0 |

TABLE 11-continued

Results of Irritation Study

Reaction by Grade

| Participant | | Repetitive Irritation Test by Observation Day | | | | | | | | | | | | | | | Average Score | Delayed Challenge | |
|---|---|---|---|---|---|---|---|---|---|---|---|---|---|---|---|---|---|---|---|
| Sex | Age | 1 | 2 | 3 | 4 | 5 | 6 | 7 | 8 | 9 | 10 | 11 | 12 | 13 | 14 | 15 | Average Score | | |
| M | 23 | 0 | 0 | 0 | 0 | 0 | 0 | 0 | 0 | 0 | 0 | 0 | 0 | 0 | 0 | 0 | 0 | 0 | 0 |
| M | 68 | 0 | 0 | 0 | 0 | 0 | 0 | 0 | 0 | 0 | 0 | 0 | 0 | 0 | 0 | 0 | 0 | 0 | 0 |
| F | 78 | 0 | 0 | 0 | 0 | 0 | 0 | 0 | 0 | 0 | 0 | 0 | 0 | 0 | 0 | 0 | 0 | 0 | 0 |
| F | 29 | 0 | 0 | 0 | 0 | 0 | 0 | 0 | 0 | 0 | 0 | 0 | 0 | 0 | 0 | 0 | 0 | 0 | 0 |
| F | 82 | 0 | 0 | 0 | 0 | 0 | 0 | 0 | 0 | 0 | 0 | 0 | 0 | 0 | 0 | 0 | 0 | 0 | 0 |
| F | 80 | 0 | 0 | 0 | 0 | 0 | 0 | 0 | 0 | 0 | 0 | 0 | 0 | 0 | 0 | 0 | 0 | 0 | 0 |
| F | 40 | 0 | 0 | 0 | 1 | 1 | 0 | 0 | 0 | 0 | 0 | 0 | 0 | 0 | 0 | 1 | 0.13 | 0 | 0 |
| F | 30 | 0 | 0 | 0 | 0 | 0 | 0 | 1 | 0 | 0 | 0 | 0 | 0 | 0 | 0 | 0 | 0.07 | 0 | 0 |
| M | 30 | 0 | 0 | 0 | 0 | 0 | 0 | 0 | 0 | 0 | 0 | 0 | 0 | 0 | 0 | 0 | 0 | 0 | 0 |
| F | 78 | 0 | 0 | 0 | 0 | 0 | 0 | 0 | 0 | 0 | 1 | 1 | 1 | 0 | 0 | 0 | 0.2 | 0 | 0 |
| F | 78 | 0 | 0 | 0 | 0 | 0 | 0 | 0 | 0 | 0 | 0 | 0 | 0 | 0 | 0 | 0 | 0 | 0 | 0 |
| M | 30 | 0 | 0 | 0 | 1 | 1 | 0 | 0 | 0 | 0 | 0 | 0 | 0 | 0 | 0 | 0 | 0.13 | 0 | 0 |
| TOTALS - Grade 1 Reactions | | 0 | 0 | 0 | 2 | 4 | 1 | 2 | 0 | 1 | 1 | 1 | 1 | 0 | 0 | 2 | | 0 | 0 |
| TOTALS - Grade 2 Reactions | | 0 | 0 | 0 | 0 | 0 | 0 | 0 | 0 | 0 | 0 | 0 | 0 | 0 | 0 | 0 | | 0 | 0 |
| TOTALS - Grade 3 Reactions | | 0 | 0 | 0 | 0 | 0 | 0 | 0 | 0 | 0 | 0 | 0 | 0 | 0 | 0 | 0 | | 0 | 0 |
| Average Irritancy Score for Product | | | | | | | | | | | | | | | | | 0.04 | | |

Table 11 shows that Formula 5 has virtually no irritation, with an average irritancy score of 0.04.

Example 7

Example 7 tested the level of irritation caused by the quaternary ammonium compound sanitizer composition of the invention. Formula 5 was used for this example. Thirty-one patients participated in this study. For this test, 0.2 ml of Formula 5 was placed on the participants upper back between the scapula and allowed to remain for at least 30 seconds but not more than 1 minute. The participants evaluated Formula 5 on a scale of 0 to 4. Table 12 explains the evaluation scale.

TABLE 12

Irritancy Scale

| Level | Definition |
|---|---|
| 0 | No visible reaction and/or erythema. |
| 1 | Slight, confluent, or patchy erythema |
| 2 | Mild reaction - macular erythema (faint, but definite pink) |
| 3 | Moderate reaction - macular erythema (definite redness, similar to sunburn) |
| 4 | Strong to severe reaction - macular erythema (very intense redness) |

The results of the irritation study are in Table 13.

TABLE 13

Results of Irritation Study

Irritancy Score

| Participant | Application Number | | | | | | | | | Challenge | |
|---|---|---|---|---|---|---|---|---|---|---|---|
| | 1 | 2 | 3 | 4 | 5 | 6 | 7 | 8 | 9 | A | B |
| 1 | 0 | 0 | 0 | 0 | 0 | 0 | 0 | 0 | 0 | 0 | 0 |
| 2 | 0 | 0 | 0 | 0 | 0 | 0 | 0 | 0 | 0 | 0 | 0 |
| 3 | 0 | 0 | 0 | 0 | 0 | 0 | 0 | 0 | 0 | 0 | 0 |
| 4 | 0 | 0 | 0 | 0 | 0 | 0 | 0 | 0 | 0 | 0 | 0 |
| 5 | 0 | 0 | 0 | 0 | 0 | 0 | 0 | 0 | 0 | 0 | 0 |
| 6 | 0 | 0 | 0 | 0 | 0 | 0 | 0 | 0 | 0 | 0 | 0 |
| 7 | 0 | 0 | 0 | 0 | 0 | 0 | 0 | 0 | 0 | 0 | 0 |
| 8 | 0 | 0 | 0 | 0 | 0 | 0 | 0 | 0 | 0 | 0 | 0 |
| 9 | 0 | 0 | 0 | 0 | 0 | 0 | 0 | 0 | 0 | 0 | 0 |
| 10 | 0 | 0 | 0 | 0 | 0 | 0 | 0 | 0 | 0 | 0 | 0 |
| 11 | 0 | 0 | 0 | 0 | 0 | 0 | 0 | 0 | 0 | 0 | 0 |
| 12 | 0 | 0 | 0 | 0 | 0 | 0 | 0 | 0 | 0 | 1 | 0 |
| 13 | 0 | 0 | 0 | 0 | 0 | 0 | 0 | 0 | 0 | 0 | 0 |
| 14 | 0 | 0 | 0 | 0 | 0 | 0 | 0 | 0 | 0 | 0 | 0 |
| 15 | 0 | 0 | 0 | 0 | 0 | 0 | 0 | 0 | 0 | 0 | 0 |
| 16 | 0 | 0 | 0 | 0 | 0 | 0 | 0 | 0 | 0 | 0 | 0 |
| 17 | 0 | 0 | 0 | 0 | 0 | 0 | 0 | 0 | 0 | 0 | 0 |
| 18 | 0 | 0 | 0 | 0 | 0 | 0 | 0 | 0 | 0 | 0 | 0 |
| 19 | 0 | 0 | 0 | 0 | 0 | 0 | 0 | 0 | 0 | 0 | 0 |
| 20 | 0 | 0 | 0 | 0 | 0 | 0 | 0 | 0 | 0 | 0 | 0 |
| 21 | 0 | 0 | 0 | 0 | 0 | 0 | 0 | 0 | 0 | 0 | 0 |
| 22 | 0 | 0 | 0 | 0 | 0 | 0 | 0 | 0 | 0 | 0 | 0 |

TABLE 13-continued

Results of Irritation Study

| | Irritancy Score | | | | | | | | | | |
|---|---|---|---|---|---|---|---|---|---|---|---|
| | Application Number | | | | | | | | | Challenge | |
| Participant | 1 | 2 | 3 | 4 | 5 | 6 | 7 | 8 | 9 | A | B |
| 23 | 0 | 0 | 0 | 0 | 0 | 0 | 0 | 0 | 0 | 0 | 0 |
| 24 | 0 | 0 | 0 | 0 | 0 | 0 | 0 | 0 | 0 | 0 | 0 |
| 25 | 0 | 0 | 0 | 0 | 0 | 0 | 0 | 0 | 0 | 0 | 0 |
| 26 | 0 | 0 | 0 | 0 | 0 | 0 | 0 | 0 | 0 | 0 | 0 |
| 27 | 0 | 1 | 0 | 0 | 0 | 0 | 0 | 0 | 1 | 0 | 0 |
| 28 | 0 | 0 | 0 | 0 | 0 | 0 | 0 | 0 | 0 | 0 | 0 |
| 29 | 0 | 0 | 0 | 0 | 1 | 1 | 0 | 1 | 1 | 0 | 0 |
| 30 | 0 | 0 | 0 | 0 | 0 | 0 | 0 | 0 | 0 | 0 | 0 |
| 31 | 0 | 0 | 1 | 0 | 0 | 0 | 0 | 0 | 0 | 0 | 0 |
| TOTALS - Grade 0 Reactions | 31 | 30 | 30 | 31 | 30 | 30 | 31 | 30 | 29 | 30 | 31 |
| TOTALS - Grade 1 Reactions | 0 | 1 | 1 | 0 | 1 | 1 | 0 | 1 | 2 | 1 | 0 |
| TOTALS - Grade 2 Reactions | 0 | 0 | 0 | 0 | 0 | 0 | 0 | 0 | 0 | 0 | 0 |
| TOTALS - Grade 3 Reactions | 0 | 0 | 0 | 0 | 0 | 0 | 0 | 0 | 0 | 0 | 0 |
| TOTALS - Grade 4 Reactions | 0 | 0 | 0 | 0 | 0 | 0 | 0 | 0 | 0 | 0 | 0 |

An average irritancy score was calculated using the following formula:

Total of induction scores/Number of evaluations/Number of subjects completing the test=Average Irritancy Score=0.0251.

A score of 0.0251 indicates that there was virtually no visible reaction and/or erythema with Formula 5.

Example 8

Example 8 compared the moisturizing effects of Formula 5 (test sites) to untreated skin (control). Seventeen females participated in this study. For this test, the participants washed their hands and forearm at least one hour prior to the application of Formula 5. Two test sites of 5 cm$^2$ were chosen on each inner forearm of the participant for a total of 60 test sites. The location of the control and the test site alternated between the two forearms. A total of 30 test sites and 30 controls were included. All readings were taking using a Courage and Khazaka (Koeln, Germany) Corneometer® Model CM 820. Baseline readings of all the 60 sites were taken prior to the product application. 0.1 ml of test product was applied to the test sites. The participants were not allowed to leave the room until the test was complete. Readings were taken of all sites at 15 minutes and 30 minutes. The average results of the 30 measurements taken are shown in Table 14.

TABLE 14

Results of Skin Moisturization Study

| Control | | | Formula 5 | | |
|---|---|---|---|---|---|
| Time | | | | | |
| Baseline | 15 minutes | 30 minutes | Baseline | 15 minutes | 30 minutes |
| 65 | 72 | 67 | 64 | 100 | 80 |

The Corneometer® measurements show a significant increase in skin moisturization with the Formula 5 test sites compared to the control sites and the baseline readings.

The foregoing summary, detailed description, and examples provide a sound basis for understanding the invention, and some specific example embodiments of the invention. Since the invention can comprise a variety of embodiments, the above information is not intended to be limiting. The invention resides in the claims.

What is claimed is:

1. A rinseless hand sanitizer composition consisting of:
   a. a quaternary ammonium compound wherein the quaternary ammonium compound exhibits antimicrobial activity;
   b. a thickener in an amount effective to provide a viscosity from about 200 to about 5,000 centipoise;
   a solvent; and
   d. optionally an additional functional ingredient selected from the group consisting of pH adjuster, skin conditioner, drying time enhancer, dye, fragrance and mixtures thereof;
   wherein the composition has less than about 30 wt. % of an alcohol.

2. The composition of claim 1, wherein the quaternary ammonium compound is selected from the group consisting of monoalkyldimethylbenzyl ammonium salts, dialkyldimethyl ammonium salts, polysubstituted quaternary ammonium salts, bis-quaternary ammonium salts, and mixtures thereof.

3. The composition of claim 2, wherein the quaternary ammonium compound is selected from the group consisting of benzalkonium chloride and benzethonium chloride.

4. The composition of claim 1, wherein the thickener is selected from the group consisting of polyacrylic acid copolymer and hydroxypropyl methylcellulose.

5. The composition of claim 1, wherein the solvent is selected from the group consisting of water, ethanol, and isopropanol.

6. The composition of claim 1, wherein the quaternary ammonium compound is present from about 0.01 wt. % to about 3 wt. %.

7. The composition of claim 1, wherein the thickener is present from about 0.001 wt. % to about 5 wt. %.

8. The composition of claim 1, wherein the solvent is present from about 25 wt. % to about 99 wt. %.

9. The composition of claim 1, wherein the quaternary ammonium compound, the thickener, and the solvent are considered to be food additives.

10. A method of reducing bacteria on a user's skin comprising:
   a. providing a rinseless hand sanitizing composition consisting of:
      i. a quaternary ammonium compound, wherein the quaternary ammonium compound exhibits antimicrobial activity;
      ii. a thickener in an amount effective to provide a viscosity from about 200 to about 5,000 centipoise;
      iii. a solvent; and
      iv. optionally an additional functional ingredient selected from the group consisting of pH adjuster skin conditioner, driving time enhancer, dye, fragrance, and mixtures thereof;
   wherein the composition has less than about 30 wt. % of an alcohol;
   b. applying the composition to a user's hands; and
   c. rubbing the composition on the user's hands, wherein at least part of the composition evaporates off of the user's hands.

11. A method of reducing bacteria on a user's hands comprising:
   a. providing a skin cleansing composition;
   b. applying the skin cleansing composition to the user's hands;
   c. applying water to the user's hands;
   d. mixing the skin cleansing composition and water together on the user's hands;
   e. rinsing the skin cleaning composition off of the user's hands;
   f. providing a hand sanitizing composition consisting of:
      i. a quaternary ammonium compound;
      ii. a thickener in an amount effective to provide a viscosity from about 200 to about 5,000 centipoise;
      iii. a solvent; and
      iv. optionally, an additional functional ingredient selected from the group consisting of pH adjuster, skin conditioner, drying time enhancer, dye, fragrance, and mixtures thereof;
   wherein the composition has less than 30 wt. % of an alcohol;
   applying the hand sanitizing composition to the user's hands; and
   rubbing the user's hands together, wherein at least part of the composition evaporates off of the user's hands.

* * * * *

UNITED STATES PATENT AND TRADEMARK OFFICE
CERTIFICATE OF CORRECTION

PATENT NO.         : 7,112,559 B1                                         Page 1 of 1
APPLICATION NO. : 11/079693
DATED              : September 26, 2006
INVENTOR(S)        : Jennifer Mayhall et al.

It is certified that error appears in the above-identified patent and that said Letters Patent is hereby corrected as shown below:

Col. 24, Line 39, "a solvent; and" should be --c. a solvent; and--

Signed and Sealed this

Eighth Day of May, 2007

JON W. DUDAS
*Director of the United States Patent and Trademark Office*